United States Patent
Cavallaro et al.

(10) Patent No.: US 9,931,062 B2
(45) Date of Patent: Apr. 3, 2018

(54) WEARABLE DEVICE SYSTEM WITH DRIVER MODE STEERING DETECTION

(71) Applicant: Motorola Mobility LLC, Chicago, IL (US)

(72) Inventors: Alberto R Cavallaro, Northbrook, IL (US); Paul B Crosbie, Grayslake, IL (US)

(73) Assignee: Motorola Mobility LLC, Chicago, IL (US)

(*) Notice: Subject to any disclaimer, the term of this patent is extended or adjusted under 35 U.S.C. 154(b) by 314 days.

(21) Appl. No.: 14/746,992

(22) Filed: Jun. 23, 2015

(65) Prior Publication Data
US 2016/0374614 A1  Dec. 29, 2016

(51) Int. Cl.
| | |
|---|---|
| *H04M 1/66* | (2006.01) |
| *G07C 5/02* | (2006.01) |
| *A61B 5/11* | (2006.01) |
| *H04M 1/725* | (2006.01) |
| *A61B 5/00* | (2006.01) |

(52) U.S. Cl.
CPC .......... *A61B 5/1122* (2013.01); *A61B 5/6898* (2013.01); *G07C 5/02* (2013.01); *H04M 1/72527* (2013.01)

(58) Field of Classification Search
CPC ................................ G07C 5/02; H04M 1/7257
See application file for complete search history.

(56) References Cited

U.S. PATENT DOCUMENTS

| | | | |
|---|---|---|---|
| 8,949,016 B1* | 2/2015 | Ferguson | B60W 30/00 340/436 |
| 8,989,914 B1* | 3/2015 | Nemat-Nasser | G06F 7/00 340/988 |
| 9,037,125 B1* | 5/2015 | Kadous | H04M 1/72577 455/418 |
| 9,630,628 B2* | 4/2017 | Holub | B60W 40/08 |
| 9,638,537 B2* | 5/2017 | Abramson | G01C 21/3626 |
| 9,744,905 B1* | 8/2017 | Assam | B60Q 9/00 |
| 9,818,239 B2* | 11/2017 | Pal | G07C 5/02 |
| 2009/0103815 A1 | 4/2009 | Inada et al. | |
| 2011/0133919 A1 | 6/2011 | Evarts et al. | |

(Continued)

OTHER PUBLICATIONS

Leon Stenneth, Ouri Wolfson, Philip S. Yu, Bo Xu, "Transportation Mode Detection Using Mobile Phones and GIS Information," ACM SIGSPATIAL GIS '11, pp. 54-63 ( Chicago, IL, Nov. 1-4, 2011).

(Continued)

*Primary Examiner* — Evan Pert
(74) *Attorney, Agent, or Firm* — Cygan Law Offices P.C.; Joseph T. Cygan

(57) ABSTRACT

A system and method of operation involves collecting acceleration and gyroscope data from a first sensor positioned in a wearable device on a user's wrist and a second sensor located in a mobile device. The mobile device determines a trajectory for the wearable device by filtering the first sensor data using the second sensor data, and determines a probability of the user holding an automobile steering wheel using the trajectory. The method may also include determining a probability of the user holding an automobile steering wheel of a specific automobile selected from an automobile list. The disclosed system includes the wearable device and the mobile device.

20 Claims, 5 Drawing Sheets

(56) References Cited

U.S. PATENT DOCUMENTS

| | | | |
|---|---|---|---|
| 2013/0024071 A1 | 1/2013 | Sivertsen | |
| 2014/0176426 A1* | 6/2014 | Morohoshi | G04R 20/26 |
| | | | 345/156 |
| 2014/0278229 A1 | 9/2014 | Hong et al. | |
| 2015/0025917 A1* | 1/2015 | Stempora | G06Q 40/08 |
| | | | 705/4 |
| 2015/0351681 A1* | 12/2015 | Lee | A61B 5/4806 |
| | | | 600/595 |
| 2016/0028267 A1* | 1/2016 | Lee | H02J 7/025 |
| | | | 320/108 |
| 2016/0216130 A1* | 7/2016 | Abramson | G01C 21/3626 |
| 2016/0318521 A1* | 11/2016 | Nothacker | B60W 40/08 |
| 2017/0053461 A1* | 2/2017 | Pal | G07C 5/02 |
| 2017/0126880 A1* | 5/2017 | Kadous | H04M 1/72577 |
| 2017/0146801 A1* | 5/2017 | Stempora | G02B 27/0172 |
| 2017/0221283 A1* | 8/2017 | Pal | G07C 5/08 |
| 2017/0232963 A1* | 8/2017 | Pal | B60W 30/08 |
| | | | 280/801.1 |
| 2017/0234691 A1* | 8/2017 | Abramson | G01C 21/3641 |
| | | | 701/442 |
| 2017/0279957 A1* | 9/2017 | Abramson et al. | H04M 1/72577 |

OTHER PUBLICATIONS

Yu Zheng, Quannan Li, Yukun Chen, Xing Xie, Wei-Ying Ma, "Understanding Mobility Based on GPS Data," UbiComp '08, pp. 1-10 (Seoul, Korea Sep. 21-24, 2008).

\* cited by examiner

P is the probability of operating wheel
C is weight for the different variables and where $C_r + C_r + C_r = 1$
m is count for being within specified limits
M is the number of measurements

WEARABLE DEVICE SYSTEM WITH DRIVER MODE STEERING DETECTION

FIELD OF THE DISCLOSURE

The present disclosure relates generally to mobile devices including wearable devices and more particularly to methods and apparatuses for motion sensing in such devices.

BACKGROUND

Mobile communication devices are increasingly being integrated with additional sensors. These sensors provide a variety of functionality such that mobile communication devices are becoming more powerful in determining a user's context and providing meaningful actions based on the determined context.

One such context determination is in-vehicle usage. A mobile communication device can determine whether a user is in a moving vehicle or not by using sensor data from one or more of an accelerometer and audio sensor and location data. After the mobile communication device makes a determination that the user is in a vehicle, it can adjust settings for hands-free mode and to facilitate the user focusing on the road while driving.

For example, some existing mobile communication devices can announce a caller's name and read out a text message for the user if the determined context is that the user is in a vehicle. This context detection response is desirable if the user is driving a car, because it facilitates the driver keeping her eyes on the road rather than being tempted to look at the mobile communication device. In some instances, the keypad or graphical user interface (GUI) may be locked to prevent the user from texting while driving. However, if the user is a passenger in the vehicle and is not the driver, the same response would be undesirable. Unfortunately, current in-vehicle context detection methods in mobile communication devices fail to distinguish between when the user is driving a car and is only a passenger in the car. This is because the data used for this purpose appears similar with respect to detected motion and location.

DETAILED DESCRIPTION

Figure 1:
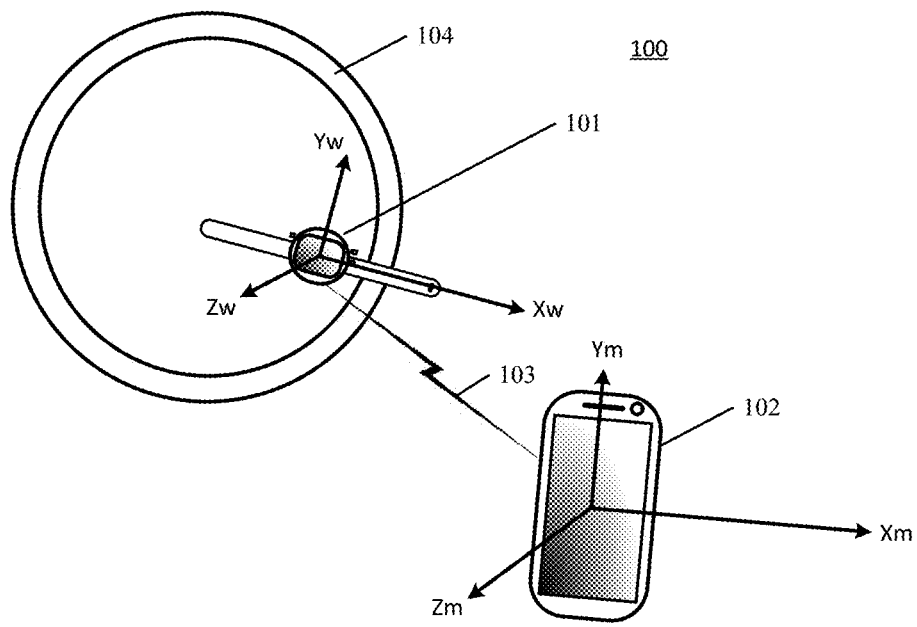
FIG. 1 is a diagram of a wearable device in communication with a mobile device for determining when a user is operating an automobile steering wheel in accordance with an embodiment.

Briefly, the present disclosure provides a system for determining drive mode for a mobile device based on movement of a wearable device. The movement of the wearable device is monitored and used to determine radius of wheel, and pitch of the wheel. Accordingly, the system may also identify a specific automobile such that the system can enable features or functions related to the specific automobile. Among other advantages, this capability can be useful in situations where the user has more than one automobile.

The disclosed embodiments provide a system that includes a wearable device, such as a smartwatch, and a mobile device such as a smartphone. The wearable device and the mobile device are configured such that they are operative to perform the methods of operation herein disclosed. A first disclosed method of operation includes collecting, by the mobile device, acceleration and gyroscope data from a first sensor positioned in the wearable device on a user's wrist and a second sensor located in the mobile device, determining a trajectory by filtering the first sensor data using the second sensor data, and determining a probability of the user holding an automobile steering wheel using the trajectory. The method may also include determining a probability of the user holding an automobile steering wheel of a specific automobile using the trajectory. In some embodiments, the specific automobile may selected from an automobile list.

A method of determining the probability of the user holding an automobile steering wheel using the trajectory includes counting the number of occurrences per number of measurements of the acceleration and gyroscope data, in which radius of curvature, and angular speed orthogonal to the radio of curvature, are within specified upper and lower limits, and assigning the probability as a sum of addends comprising the weighted occurrences. The method may also include assigning the probability as a sum of addends comprising the weighted occurrences, wherein one of the addends is a steering wheel tilt angle. In the disclosed methods of operation, weighting factors may be assigned to addends including radius of curvature, angular speed orthogonal to the radius of curvature, and steering wheel tilt angel where the sum of the weighting factors is equal to one.

The trajectory may be obtained by determining an acceleration vector and a rotation rate vector for the wearable device using the first sensor acceleration and gyroscope data, and correcting the acceleration vector and the rotation rate vector for the wearable device using the second sensor acceleration and gyroscope data. The method may further include subtracting gravitational effects from the acceleration vector and the rotation rate vector for the wearable device. A radius and an angular speed are calculated using the acceleration vector and the rotation rate vector. A steering wheel tilt angle may also be determined using the first sensor acceleration and gyroscope data.

One method for determining the trajectory includes establishing a time series equation with an acceleration vector and a rotation rate vector for the wearable device containing the first sensor and for the mobile device, inputting the acceleration and gyroscope data from the first sensor and from the second sensor into the time series equation, calculating a gravity unit vector for the wearable device and for the mobile device using the time series equation, and calculating a relative acceleration vector and a relative rotation rate vector for the wearable device and for the mobile device.

A disclosed mobile device in one embodiment includes an accelerometer; peer-to-peer baseband hardware, operatively coupled to at least one antenna; and a processor, operatively coupled to the accelerometer and to the peer-to-peer baseband hardware. The processor is operative to: collect wearable device acceleration and gyroscope data as first sensor data from a first sensor positioned in a wearable device using a wireless interface implemented using the peer-to-peer baseband hardware, and mobile device acceleration data as second sensor data from the accelerometer; determine a trajectory by filtering the first sensor data using the second sensor data; and determine a probability of the wearable device user holding an automobile steering wheel using the trajectory.

The mobile device may further include non-transitory, non-volatile memory, operatively coupled to the processor and having an automobile list stored therein. The processor may be further operative to determine a probability of the wearable device user holding an automobile steering wheel of a specific automobile using the trajectory, where the specific automobile is selected from the automobile list.

Turning now to the drawings, FIG. 1 is a diagram of a wearable device 101 in communication with a mobile device 102 for determining when a user is operating an automobile steering wheel 104 in accordance with an embodiment. The system 100 includes the wearable device 101 which may be a smartwatch and the mobile device 102 which may be a smartphone. A first sensor contained within the wearable device 101 includes a gyroscope and accelerometer function and is operative to send motion data to the mobile device 102 using a wireless interface 103. The wireless interface 103 may be any suitable wireless interface used for tethering devices such as, but not limited to Bluetooth®, IEEE 802.11x (WiFi®) or similar wireless interfaces.

When the user is wearing the wearable device 101 and operates the automobile steering wheel 104, the first sensor within the wearable device 101 senses the linear acceleration along the x, y and z axes and the angular velocities about these axes of the wearable device 101 and determines orientation and motion and sends this information to the mobile device 102. The mobile device 102 includes a second sensor which also includes a gyroscope and accelerometer function, and also begins to collect motion data from its own second sensor. The mobile device 102 runs a method of operation, or process, where the first sensor data is corrected by the second sensor data of the mobile device 102 in order to determine that the user is operating the steering wheel 104.

Figure 2:
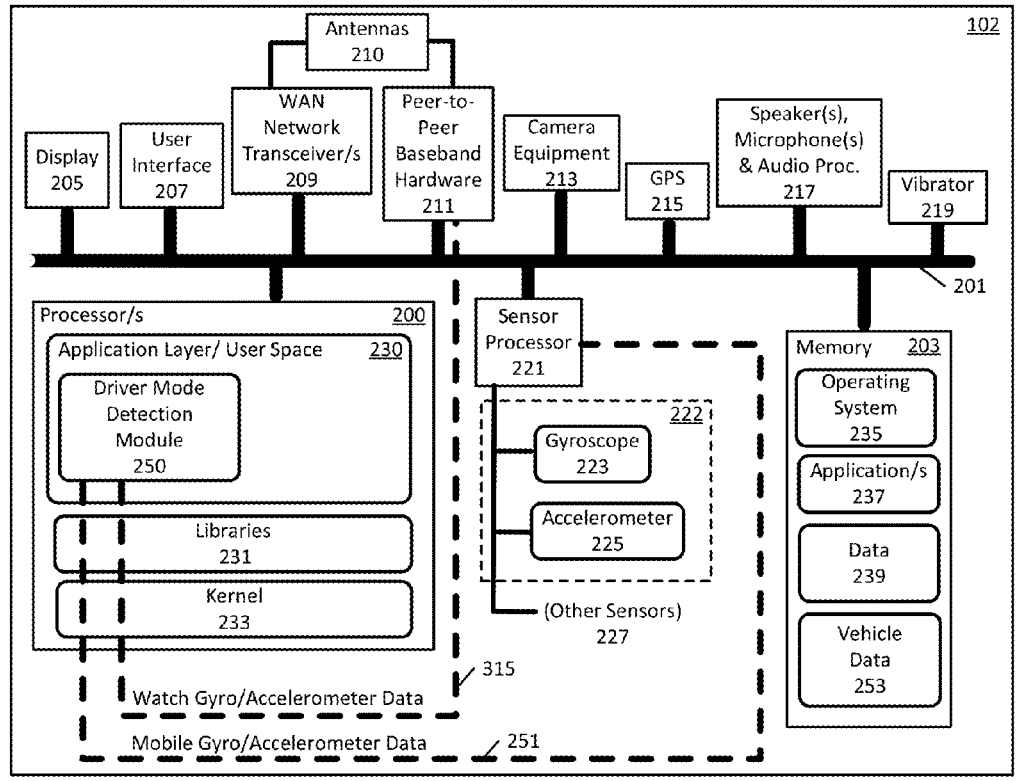
FIG. 2 is block diagram of a mobile device in communication in accordance with an embodiment.

Further details of an example embodiment of the mobile device 102 are provided in FIG. 2. The mobile device 102 includes one or more processors 200, memory 203, a display 205, user interface 207, one or more wide area network (WAN) transceivers 209 (such as, but not limited to CDMA, UMTS, GSM, etc.), peer-to-peer baseband hardware 211 (which includes transceivers) for implementing the wireless interface 103, one or more antennas 210, camera equipment 213, GPS hardware 215, speakers, microphones and audio processing 217, a vibrator unit 219, and a sensor processor 221. All of the components shown are operatively coupled to the one or more processors 200 by one or more internal communication buses 201.

The sensor processor 221 monitors sensor data from various sensors including a gyroscope 223 and an accelerometer 225 as well as other sensors 227. The gyroscope 223 and accelerometer 225 may be separate or may be combined into a single integrated unit, i.e. a single sensor 222. In some embodiments, the gyroscope 223 may not be present and only the accelerometer 225 data may be used. Speakers, microphones and audio processing 217 may include, among other things, at least one microphone, at least one speaker, signal amplification, analog-to-digital conversion/digital audio sampling, echo cancellation, etc., which may be applied to one or more microphones and/or one or more speakers of the mobile device 102.

The memory 203 is non-volatile and non-transitory and stores executable code for an operating system 235 that, when executed by the one or more processors 200, provides an application layer (or user space) 230, libraries 231 (also referred to herein as "application programming interfaces" or "APIs") and a kernel 233. The memory 203 also stores executable code for various applications 237, data 239 and vehicle data 253 in some embodiments. The memory 203 may be operatively coupled to the one or more processors 200 via the internal communications buses 201 as shown, may be integrated with the one or more processors 200, or may be some combination of operatively coupled memory and integrated memory.

The one or more processors 200 are operative to launch and execute the applications 237 including a driver mode detection module 250 in accordance with an embodiment. However it is to be understood that the driver mode detection module 250 can be implemented in other ways that are contemplated by the present disclosure and that the example shown in FIG. 2 is only one possible implementation. For example the driver mode detection module 250 may be implemented in hardware or as a combination or hardware and software and/or firmware.

The driver mode detection module 250 is operatively coupled to the peer-to-peer baseband hardware 211 and is operative to obtain gyroscope and accelerometer measurements 315 from the wearable device 101. In the example of FIG. 2, the one or more processors 200 are configured, by execution of the driver mode detection module 250, to be operative to send command and control signals to the wearable device 101 over the wireless interface 103, and to receive the wearable device 101 gyroscope and accelerometer data 315. The one or more processors 200 are also operative to communicate with the sensor processor 221 to obtain mobile device 102 gyroscope and accelerometer data 251 from the gyroscope 223 and accelerometer 225 (i.e. from sensor 222). In some embodiments, the driver mode detection module 250 may run as a background application and may wait until the driver mode detection module 250 or the wearable device 101 detects motion before it begins to collect sensor data.

In the example of FIG. 2, the driver mode detection module 250 is shown implemented as executable instructions executed by the one or more processors 200 that configure the one or more processors 200 to perform the methods of operation according to the embodiments. However, it is to be understood that the driver mode detection module 250 may be implemented as hardware, or as a combination of hardware and software/firmware. In embodiments where the driver detection module 250 is implemented as software, or partially in software/firmware, the executable instructions may be stored in the operatively coupled, non-volatile, non-transitory memory 203, which may be accessed by the one or more processors 200 as needed.

It is to be understood that various other of the above described example components in the example mobile device 102 may be implemented as software (i.e. executable instructions or executable code) or firmware (or a combination of software and firmware) executing on one or more processors, or using ASICs (application-specific-integrated-circuits), DSPs (digital signal processors), hardwired circuitry (logic circuitry), state machines, FPGAs (field programmable gate arrays) or combinations thereof. Therefore the mobile device 102 illustrated in FIG. 2 and described herein provides just one example embodiment and is not to be construed as a limitation on the various other possible implementations that may be used in accordance with the various embodiments.

As further examples, the driver mode detection module 250 may be implemented as any combination of DSPs, ASICs, FPGAs, CPUs running executable instructions, hardwired circuitry, state machines, etc., without limitation. Therefore, as one example embodiment, the driver mode detection module 250 may be implemented using an ASIC or an FPGA that may be operatively coupled to the one or more processors 200. These example embodiments and other embodiments are contemplated by the present disclosure.

Figure 3:
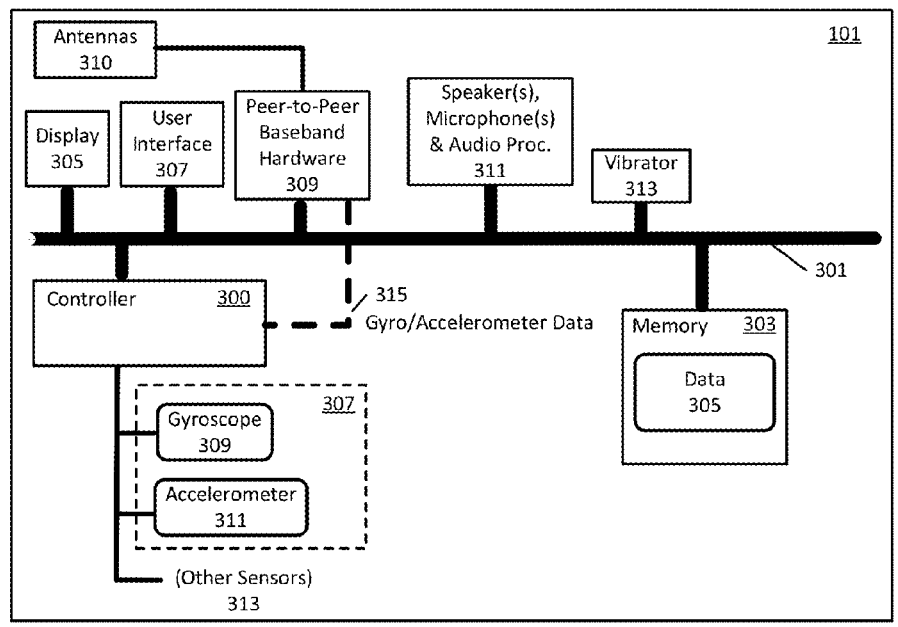
FIG. 3 is block diagram of a wearable device in accordance with an embodiment.

FIG. 3 is block diagram of the wearable device 101 in accordance with an embodiment. The wearable device 101 includes some components that are similar to the components of the mobile device 102. For example, the wearable device 101 may include display 305, user interface 307, peer-to-peer baseband hardware 309, antennas 310 operatively coupled to the peer-to-peer baseband hardware 309, speakers microphone and audio processing 311, a vibrator unit 313, and a controller 300. The controller 300 is operatively coupled to the above components by an internal communication bus 301. The wearable device 101 may also include a memory 303.

The controller 300 is operatively coupled to a sensor 307, which includes a gyroscope 309 and an accelerometer 311. The controller 300 is operative to send sensor 307 data (i.e. gyroscope and accelerometer data 315) to the peer-to-peer baseband hardware 309 such that it can be sent to the mobile device 102 over the wireless interface 103. The wearable device 101 may also include other sensors 313 such as, but not limited to, capacitive touch sensors, light sensors, other proximity sensors, temperature sensors, etc. In some embodiments, the gyroscope 309 and accelerometer 311 may be separate sensors or may be integrated into the single sensor 307 similar to the sensor 222 described with respect to the mobile device 102 and FIG. 2.

The controller 300 is operative to gather gyroscope and accelerometer data 315 and, in some embodiments, may initially detect motion prior to starting data gathering. The controller 300 is operative to receive command-and-control signals, from the processor 200 of mobile device 102, over the wireless interface 103 by way of the peer-to-peer baseband hardware 309 and antennas 310. These command-and-control signals may, among other things, command the controller 300 to begin to collect the gyroscope and accelerometer data 315 and to transmit the gyroscope and accelerometer data 315 to the mobile device 102. The gyroscope accelerometer data 315 may be collected at fixed intervals of time so as to collect a specified number of measurements specified by the processor 200 of the mobile device 102.

The memory 303 is a non-volatile non-transitory memory and may include data 305 which may be user settings, or in some embodiments may contain settings related to the automobile. For example, when the system 100 of the wearable device 101 and the mobile device 102 determines that the user is operating the steering wheel of a specific automobile, the system 100, via either the wearable device 101 or the mobile device 102, may adjust settings of the automobile using the same wireless interface 103 used for communication between the wearable device 101 and the mobile device 102, and may send command-and-control information to an automobile setting system so as to perform certain operations. For example, the wearable device 101 or the mobile device 102 may send a command to the automobile control system to adjust the height and settings of the driver seat such that the driver seat setting preferences (stored in memory 303 as data 305) are set accordingly. Other settings of the automobile may also be adjusted using the wireless interface based on the system 100 having detected that the user is operating the specific automobile.

Figure 4:
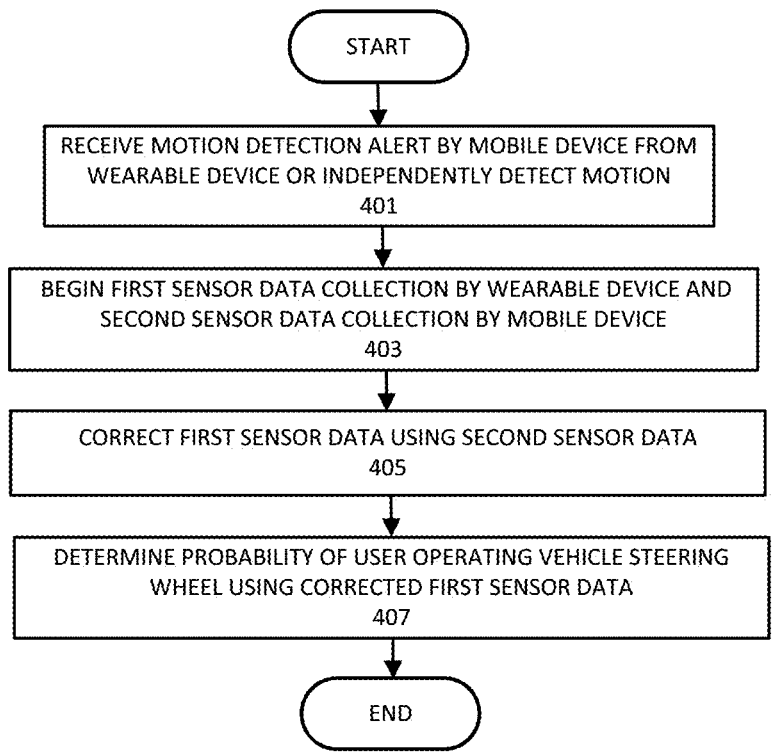
FIG. 4 is a flow chart of a process in a wearable device and a mobile device in accordance with various embodiments.

FIG. 4 is a flow chart of a method of operation of the system 100 in accordance with various embodiments. In operation block 401, mobile device 102 either receives an alert from the wearable device 101 that motion has been detected, or the mobile device 102 independently detects motion. This may occur for example, when the user starts the ignition of the automobile and begins to move the vehicle out of a parking space. In operation block 403, the wearable device 101 will begin first sensor data collection and the mobile device 102 will begin second sensor data collection. As discussed previously, the first sensor and the second sensor include gyroscope and accelerometer capabilities. However in some embodiments, the second sensor of the mobile device 102 may be an accelerometer only. A Fourier transform of the data collected in operation block 403 may be used to determine the gravity plane for both the mobile device 102 and the wearable device 101. In operation block 405, mobile device 102 corrects the first sensor data using the second sensor data. In operation block 407, mobile device 102 determines the probability of the user operating the vehicle steering wheel 104 using the corrected first sensor data. The method of operation then ends as shown. The operations attributed to the mobile device 102 may be performed by the one or more processors 200 and, more particularly, the driver mode detection module 250.

Therefore, a first set of measurements is obtained from the wearable device 101 and a second set of measurements is obtained from the mobile device 102. The mobile device 102 gyroscope and accelerometer data 251 can provide data related to the angular velocity and, because it is likely positioned on the car seat or elsewhere in the vehicle, can provide data to help eliminate forces caused by vehicle movement or other additional external forces. A radius vector is calculated such that a steering wheel size and tilt may be determined.

Figure 5:
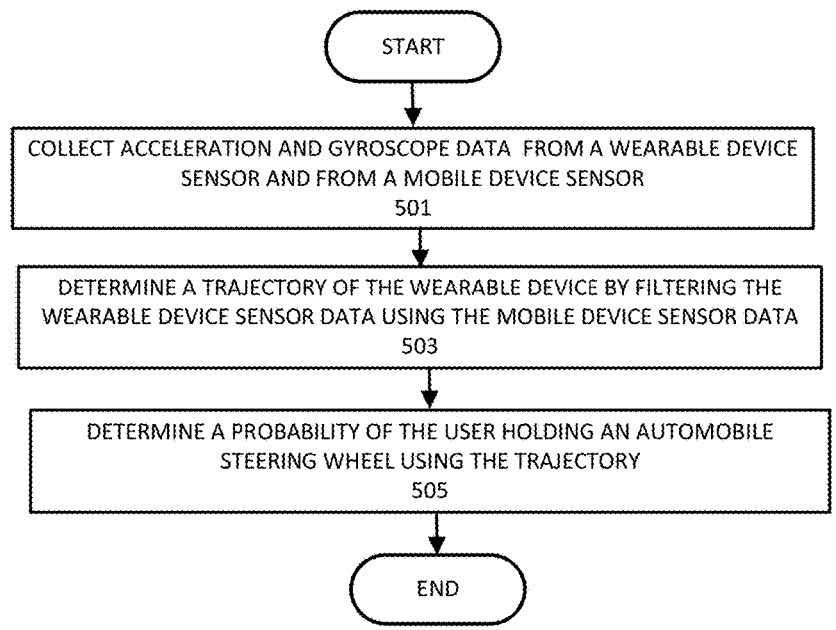
FIG. 5 is a flow chart of a process in a mobile device in accordance with an embodiment.

Turning to FIG. 5, a flow chart of a method of operation in the mobile device 102 in accordance with an embodiment is provided. In operation block 501, the one or more processors 200 collect gyroscope and accelerometer data from the wearable device 101 sensor 307 and from the mobile device 102 sensor 222. In operation block 503, the one or more processors 200 determine a trajectory of the wearable device 101 by filtering the wearable device 101 sensor data using the mobile device 102 sensor data. In operation block 505, the one or more processors 200 determine a probability of the user holding the automobile steering wheel 104 by using the trajectory. The method of operation then ends as shown.

Figure 6:
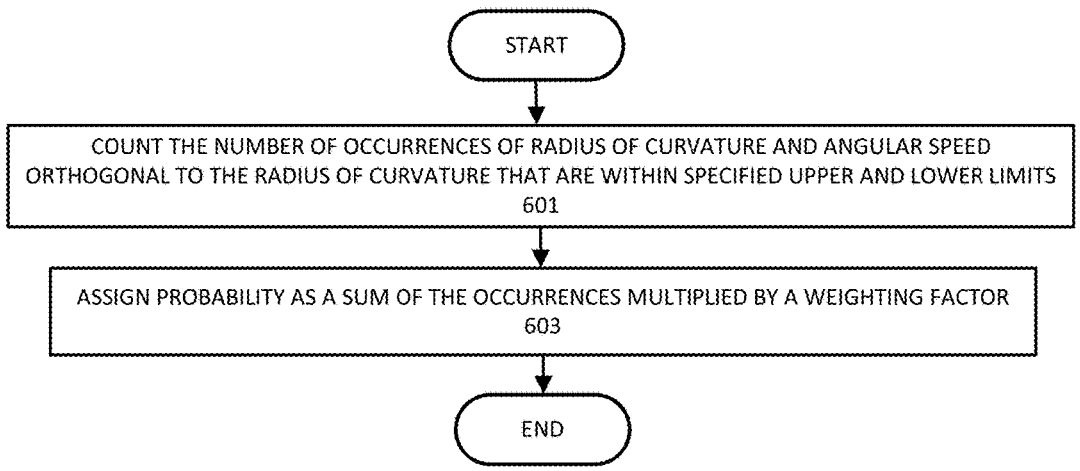
FIG. 6 is a flowchart of a process in a mobile device in accordance with an embodiment.

FIG. 6 is a flowchart of another method of operation in the mobile device 102 in accordance with an embodiment. In operation block 601, the one or more processors 200 count the number of occurrences of radius of curvature and angular speed orthogonal to the radius of curvature that are within specified upper and lower limits. In operation block 603, the one or more processors 200 assign probability as a summation of the occurrences multiplied by a weighting factor. The method of operation then ends as shown.

Figure 7:
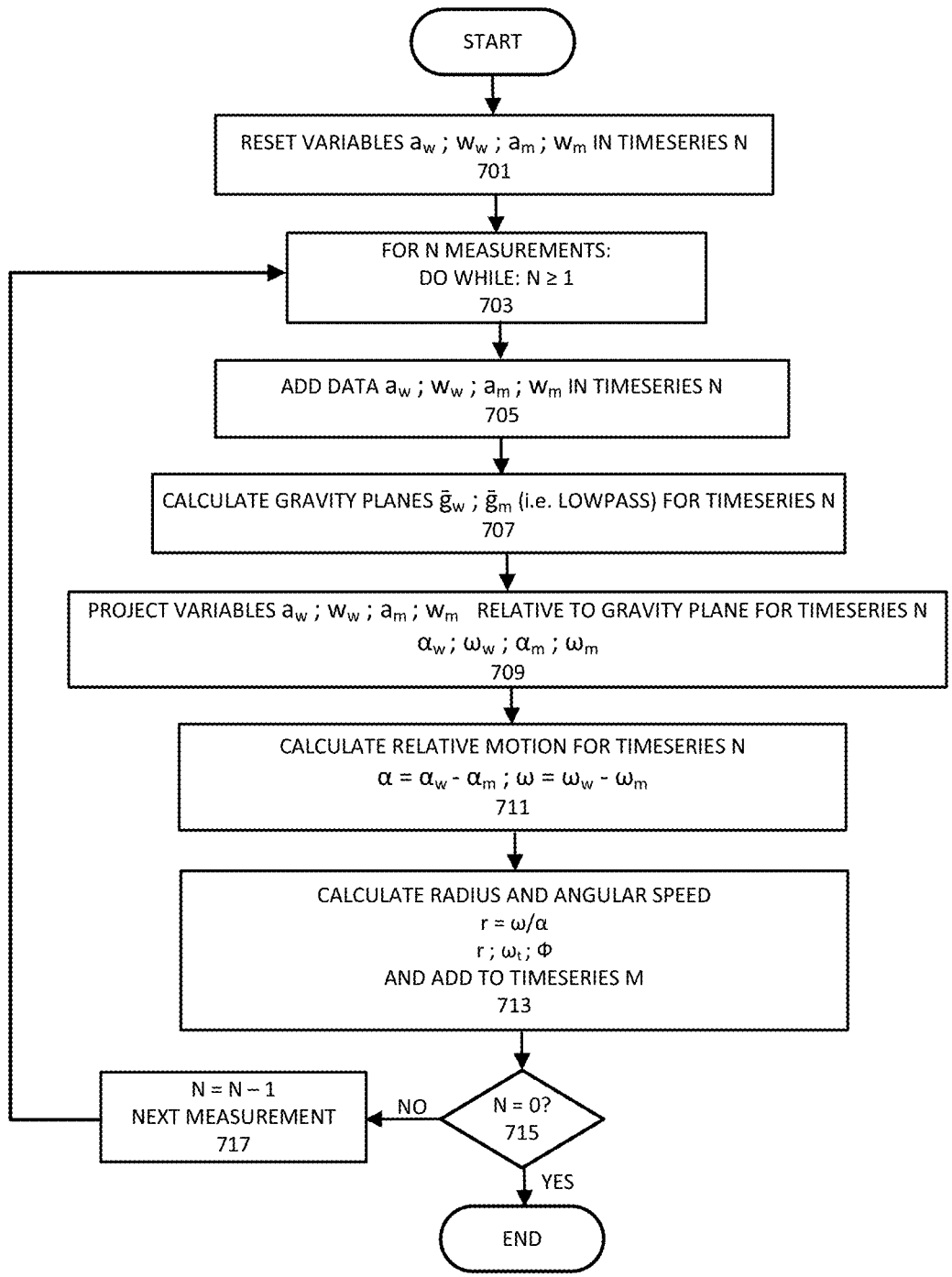
FIG. 7 is a flow chart of a process in a mobile device for determining a trajectory in accordance with an embodiment.

FIG. 7 is a flow chart providing a detailed example method of operation in a mobile device for determining a trajectory in accordance with an embodiment. For brevity within the flowchart operation blocks, the following variables have been used and are defined as follows: "$a_w$" and "$a_m$" are the acceleration vectors of the wearable device and the mobile device, respectively; "$w_w$" and "$w_m$" are the rotation rate vectors of the wearable device and the mobile device, respectively; "$\bar{g}_w$" and "$\bar{g}_m$" are the gravity unit vectors of the wearable device and the mobile device, respectively; "$\alpha_w$" and "$\alpha_m$" are the acceleration vectors relative to the gravity plane for the wearable device and the mobile device, respectively; "$\omega_w$" and "$\omega_m$" are the rotation rate vectors relative to the gravity plane for the wearable device and the mobile device, respectively; "N" represents a timeseries equation for angular speed and radius calculation; "M" represents a timeseries equation for angular speed and radius results; "r" is the radius of curvature; "$\omega_t$" is the angular speed orthogonal to the radius of curvature; and "Φ" represents the tile angle of the steering wheel.

In operation block 701, a first time series "N" is established and the variables representing the acceleration vectors $a_w$ and $a_m$ and rotation rate vectors $w_w$ and $w_m$ are reset. In operation block 703, the driver mode detection module 250 begins to perform a looping operation for "N" number of measurements and performs the operation while the index "N" is greater than or equal to one. In looping operation may begin in response to detection of motion by the driver mode detection module 250 or by a wireless signal from the wearable device 101 when the controller 300 detects motion.

In operation block 705, data is collected from the wearable device 101 sensor 307 and from the mobile device 102 sensor 222 and the data is added into the time series accordingly. In operation block 707, the driver mode detection module 250 calculates gravity planes for the time series and determines the gravity unit vectors $\bar{g}_w$ and $\bar{g}_m$ for wearable device 101 and for the mobile device 102, respectively. In operation block 709, the variables $a_w$, $a_m$, $w_w$ and $w_m$, are projected relative to the calculated gravity plane for the time series resulting in $\alpha_w$, $\alpha_m$, $\alpha_w$ and $\alpha_m$ and, in operation block 711, the driver mode detection module 250 calculates relative motion for the time series and where the corrected acceleration vector "α" is determined by subtracting the mobile device vector $\alpha_m$ from the wearable device vector $\alpha_w$. More specifically, the relative acceleration vector is equal to the acceleration vector of the wearable device 101 relative to the gravity unit vector for the wearable device 101, minus the acceleration vector of the mobile device 102 relative to the gravity unit vector for the mobile device 102. Likewise the corrected rotation rate vector "ω" is equal to the rotation rate vector of the wearable device 101 relative to the gravity plane, i.e. $\omega_w$, minus the rotation rate vector of the mobile device 102 relative to the gravity plane, i.e. $\omega_m$.

In operation block 713, the driver mode detection module 250 calculates the radius "r" and angular speed "$\omega_t$" and adds the radius and angular speed to the time series "M." In decision block 715, the index of the number of measurements is checked such that if the index equals zero, then the method of operation ends as shown. However if the value of the index is still an integer greater than or equal to one in decision block 715, then the index is decremented by one in operation block 717, and the next measurement proceeds by looping back to operation block 701 and operation block 703 until "N" measurements have been completed.

Figure 8:
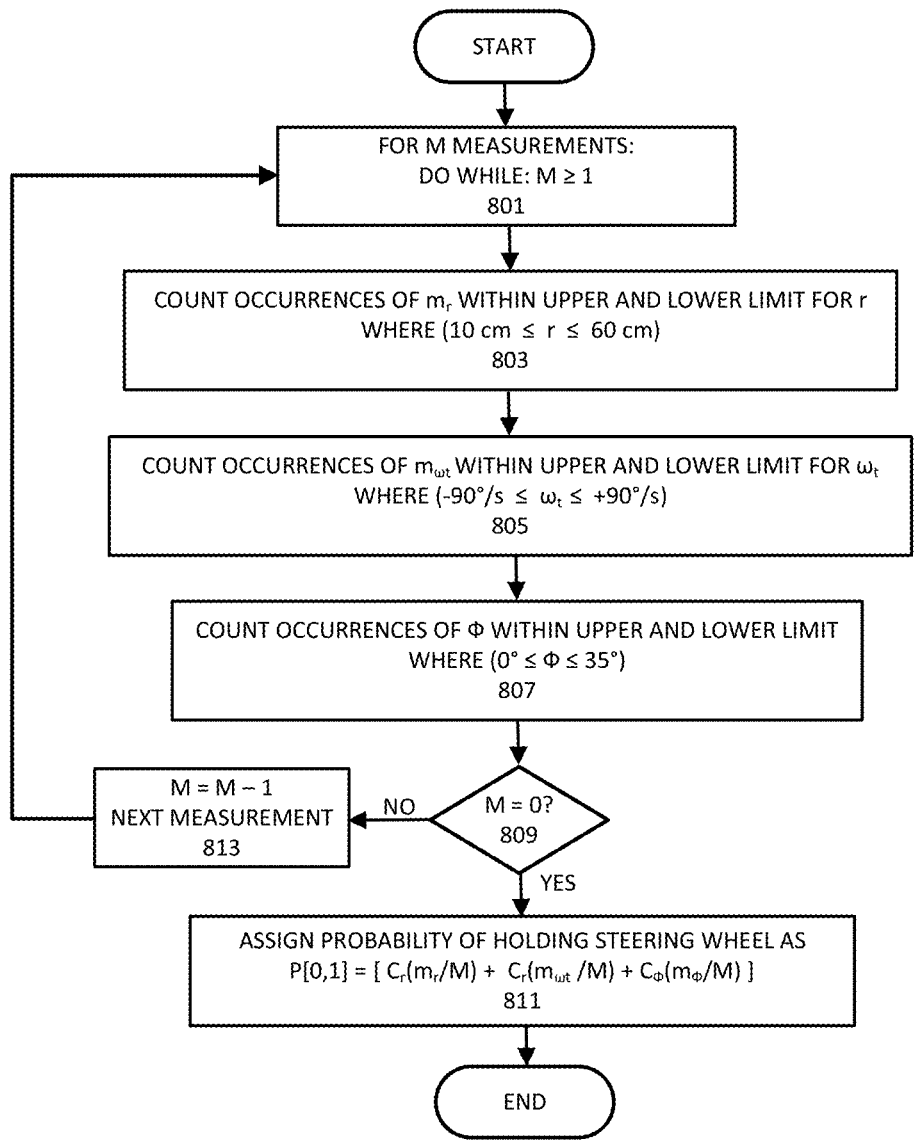
FIG. 8 is a flowchart of a process in a mobile device for determining a probability that a user is operating an automobile steering wheel in accordance with an embodiment.

FIG. 8 is a flowchart providing a detailed example method of operation in a mobile device for determining a probability that a user is operating an automobile steering wheel in accordance with an embodiment. For brevity within the flowchart operation blocks, the following variables have been used and are defined as follows: "P" is the probability of the user operating the vehicle steering wheel; "C" is a weighting factor relative to the addends where a subscript denotes the specific addend to which the weighting factor is applicable; "m" represents a count of the number of occurrences of a variable within a specified upper and lower limit, where a subscript denotes the specific variable to which the count is applicable; and "M" is the number of measurements.

Beginning in operation block 801, for M measurements, a looping operation begins and continues until M is equal to zero. In operation block 803, the driver mode detection module 250 counts occurrences of the radius of curvature "r" where the radius of curvature is within a specified upper and lower limit. For example, in one embodiment, the lower limit may be 10 cm and the upper limit may be 60 cm. In operation block 805, the driver mode detection module 250 counts occurrences of the angular speed orthogonal to the radius of curvature, $\omega_t$, where the angular speed falls within the upper and lower limit of +90° per second and −90° per second, respectively. In operation block 807, the driver mode detection module 250 counts occurrences of the tilt angle Φ that are within an upper and lower limit. For example, in one embodiment, the lower limit may be 0° and the upper limit may be 35°. In decision block 809, if the index "M" equals zero, then the method of operation proceeds to operation block 811 and assigns probability of the user holding the steering wheel as a summation of the counts per number of measurements, multiplied by appropriate weighting factors. If the number of measurements has not been reached in operation block 809, then the method of operation proceeds to operation block 813 and decrements the number of measurements by one. The method of operation then loops back to operation block 801 and operation block 803 and continues the looping operation until the number of specified measurements is completed.

While various embodiments have been illustrated and described, it is to be understood that the invention is not so limited. Numerous modifications, changes, variations, substitutions and equivalents will occur to those skilled in the art without departing from the scope of the present invention as defined by the appended claims.

What is claimed is:

1. A method comprising:
   collecting, by a mobile device, acceleration and gyroscope data from a first sensor positioned in a wearable device on a user's wrist and a second sensor located in the mobile device;
   determining a trajectory by filtering the first sensor data using the second sensor data; and
   determining a probability of the user holding an automobile steering wheel using the trajectory.

2. The method of claim 1, further comprising:
   determining a probability of the user holding an automobile steering wheel of a specific automobile using the trajectory, the specific automobile selected from an automobile list.

3. The method of claim 1, wherein determining the probability of the user holding an automobile steering wheel using the trajectory, comprises:
   counting the number of occurrences per number of measurements of the acceleration and gyroscope data, in which radius of curvature, and angular speed orthogonal to the radio of curvature, are within specified upper and lower limits; and
   assigning the probability as a sum of addends comprising the weighted occurrences.

4. The method of claim 3, further comprising:
assigning the probability as a sum of addends comprising the weighted occurrences, wherein one of the addends is a steering wheel tilt angle.

5. The method of claim 4, further comprising:
assigning weighting factors to radius of curvature addend, angular speed orthogonal to the radius of curvature, and steering wheel tilt angel where the sum of the weighting factors is equal to one.

6. The method of claim 1, wherein determining the trajectory comprises:
determining an acceleration vector and a rotation rate vector for the wearable device using the first sensor acceleration and gyroscope data; and
correcting the acceleration vector and the rotation rate vector for the wearable device using the second sensor acceleration and gyroscope data.

7. The method of claim 6, further comprising:
subtracting gravitational effects from the acceleration vector and the rotation rate vector for the wearable device.

8. The method of claim 6, further comprising:
calculating a radius and an angular speed using the acceleration vector and the rotation rate vector.

9. The method of claim 6, further comprising:
determining a steering wheel tilt angle using the first sensor acceleration and gyroscope data.

10. The method of claim 1, wherein determining the trajectory comprises:
establishing a time series equation with an acceleration vector and a rotation rate vector for the wearable device containing the first sensor and for the mobile device;
inputting the acceleration and gyroscope data from the first sensor and from the second sensor into the time series equation;
calculating a gravity unit vector for the wearable device and for the mobile device using the time series equation; and
calculating a relative acceleration vector and a relative rotation rate vector for the wearable device and for the mobile device.

11. A mobile device comprising:
an accelerometer;
peer-to-peer baseband hardware, operatively coupled to at least one antenna;
a processor, operatively coupled to the accelerometer and to the peer-to-peer baseband hardware, and operative to:
collect wearable device acceleration and gyroscope data as first sensor data from a first sensor positioned in a wearable device using a wireless interface implemented using the peer-to-peer baseband hardware, and mobile device acceleration data as second sensor data from the accelerometer;
determine a trajectory by filtering the first sensor data using the second sensor data; and
determine a probability of the wearable device user holding an automobile steering wheel using the trajectory.

12. The mobile device of claim 11, further comprising:
non-transitory, non-volatile memory, operatively coupled to the processor and having an automobile list stored therein; and
wherein the processor is further operative to:
determine a probability of the wearable device user holding an automobile steering wheel of a specific automobile using the trajectory, the specific automobile selected from the automobile list.

13. The mobile device of claim 11, wherein the processor is further operative to determine the probability of the user holding an automobile steering wheel using the trajectory, by:
counting the number of occurrences per number of measurements of the acceleration and gyroscope data, in which radius of curvature, and angular speed orthogonal to the radio of curvature, are within specified upper and lower limits; and
assign the probability as a sum of addends comprising the weighted occurrences.

14. The mobile device of claim 13, wherein the processor is further operative to:
assign the probability as a sum of addends comprising the weighted occurrences, wherein one of the addends is a steering wheel tilt angle.

15. The mobile device of claim 14, wherein the processor is further operative to:
assign weighting factors to radius of curvature addend, angular speed orthogonal to the radius of curvature, and steering wheel tilt angel where the sum of the weighting factors is equal to one.

16. The mobile device of claim 11, wherein the processor is further operative to determine the trajectory by:
determining an acceleration vector and a rotation rate vector for the wearable device using the first sensor acceleration and gyroscope data; and
correcting the acceleration vector and the rotation rate vector for the wearable device using the second sensor acceleration and gyroscope data.

17. The mobile device of claim 16, wherein the processor is further operative to:
subtract gravitational effects from the acceleration vector and the rotation rate vector for the wearable device.

18. The mobile device of claim 16, wherein the processor is further operative to:
calculate a radius and an angular speed using the acceleration vector and the rotation rate vector.

19. The mobile device of claim 16, wherein the processor is further operative to:
determine a steering wheel tilt angle using the first sensor acceleration and gyroscope data.

20. The mobile device of claim 11, wherein the processor is further operative to determine the trajectory by:
establishing a time series equation with an acceleration vector and a rotation rate vector for the wearable device containing the first sensor and for the mobile device;
inputting the acceleration and gyroscope data from the first sensor and from the second sensor into the time series equation;
calculating a gravity unit vector for the wearable device and for the mobile device using the time series equation; and
calculating a relative acceleration vector and a relative rotation rate vector for the wearable device and for the mobile device.

* * * * *